(12) United States Patent
Tucker et al.

(10) Patent No.: US 6,529,759 B1
(45) Date of Patent: Mar. 4, 2003

(54) METHOD FOR MAPPING INTERNAL BODY TISSUE

(75) Inventors: Don Tucker, Eugene, OR (US); Susan E. Tucker, Eugene, OR (US)

(73) Assignee: Electrical Geodesics, Inc., Eugene, OR (US)

(*) Notice: Subject to any disclaimer, the term of this patent is extended or adjusted under 35 U.S.C. 154(b) by 0 days.

(21) Appl. No.: 09/803,085

(22) Filed: Mar. 8, 2001

(51) Int. Cl.[7] ................................................ A61B 5/05
(52) U.S. Cl. ...................................... 600/407; 600/410
(58) Field of Search ................................ 600/407, 409, 600/410, 414, 418, 421, 425, 436, 544, 545, 547, 562, 372, 382, 384, 386, 461, 476, 477, 478; 250/272, 273, 274, 277 R, 278, 279; 378/62, 54, 19, 145, 146

(56) References Cited

U.S. PATENT DOCUMENTS

| | | | | |
|---|---|---|---|---|
| 4,123,654 A | * | 10/1978 | Reiss et al. | ............ 250/363.04 |
| 4,436,684 A | | 3/1984 | White | |
| 4,532,591 A | | 7/1985 | Osterholm | |
| 4,608,635 A | | 8/1986 | Osterholm | |
| 4,922,915 A | * | 5/1990 | Arnold et al. | ............... 600/546 |
| 5,165,410 A | * | 11/1992 | Warne et al. | .......... 250/363.04 |
| 5,291,888 A | * | 3/1994 | Tucker | ...................... 600/383 |
| 5,390,110 A | | 2/1995 | Cheney et al. | |
| 5,465,284 A | * | 11/1995 | Karellas | .................. 250/252.1 |
| 5,482,034 A | | 1/1996 | Lewis | |
| 5,630,422 A | | 5/1997 | Zanakis | |
| 5,719,399 A | | 2/1998 | Alfano et al. | |
| 5,807,251 A | | 9/1998 | Wang et al. | |
| 5,810,742 A | * | 9/1998 | Pearlman | .................... 600/547 |
| 5,813,984 A | | 9/1998 | Haaga et al. | |
| 5,853,370 A | | 12/1998 | Chance et al. | |
| 5,902,235 A | | 5/1999 | Lewis et al. | |
| 6,041,094 A | * | 3/2000 | Russell | ....................... 378/162 |
| 6,330,470 B1 | * | 12/2001 | Tucker et al. | ............... 600/544 |

\* cited by examiner

*Primary Examiner*—Tu Ba Hoang
(74) *Attorney, Agent, or Firm*—Birdwell, Janke & Durando, PLC

(57) ABSTRACT

A method for mapping internal body tissue. The method preferably includes determining the spatial distribution of bone tissue of a patient that shields target soft tissue, the structure of which it is desired to determine and monitor, and subjecting the patient to changing electric, magnetic or electromagnetic fields adapted for interacting with the target soft tissue as a function of the spatial distribution of the soft tissue. Electric, magnetic or electromagnetic energy that is transmitted through the bone and the soft tissue is analyzed to infer the spatial distribution of the soft tissue with the assistance of knowledge of the spatial distribution of the bone tissue.

8 Claims, 1 Drawing Sheet

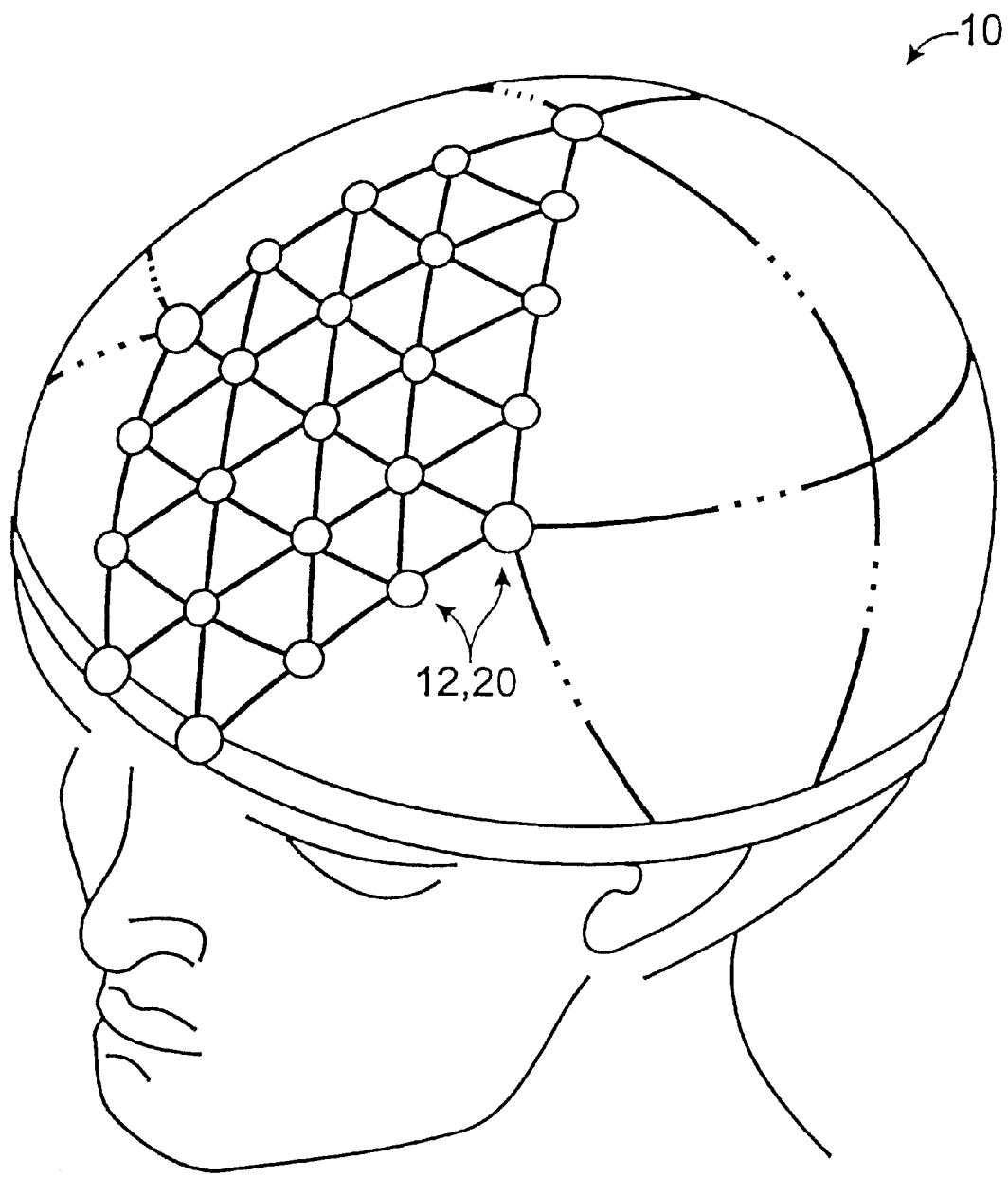

METHOD FOR MAPPING INTERNAL BODY TISSUE

BACKGROUND OF THE INVENTION

The present invention relates to a method for mapping internal body tissue, particularly body tissue inside or otherwise shielded by bone, and more particularly cranial soft tissue inside the skull.

The present inventor has recognized that at least brain soft tissue, and probably other soft tissue in the body, can exhibit changes to its structure during a short time-span, which can be as short as a few tens of milliseconds, in response to physiologic function and certain pathologies, such as a stroke or epileptic seizure. In addition, it is well known that the electric and magnetic fields produced by brain, heart or other tissue change rapidly over time in both normal and pathological function. Knowledge of these changes would therefore be useful to indicate the pathology and to monitor its progress or regress over time.

As is well known, the prior art has long used computer aided tomography ("CT"), which employs X-rays, to map interior body tissue. One readily appreciated problem with CT is that the X-rays do not provide good resolution of soft tissue. However, another major drawback of CT in the context of the aforementioned recognition is that exposure to X-rays is detrimental to health and therefore CT cannot be used for prolonged periods of time as a monitoring device.

Nuclear magnetic resonance imaging ("MRI") is another well known method for mapping internal body tissue. MRI employs strong magnetic fields that are thought not to pose a significant health risk. MRI provides excellent resolution of soft tissue and is not hindered by bone surrounding the soft tissue. On the other hand, MRI has two major drawbacks. One well known drawback is that the machines are very costly and, therefore, machine time must be rationed. However, another drawback of MRI in the context of the aforementioned recognition is that the patient must be substantially completely immobilized during the time of imaging, which also prevents its use as a method for monitoring a patient over a prolonged period of time. The present inventor has also noted that MRI as it is currently provided is not adapted to seeing the changes in structure that are indicative of brain pathologies. There is a question whether this could be done given an appropriate motivation.

Accordingly, there is a need for a method for mapping internal body tissue that provides for the ability to discern structural changes in the body tissue that occur over very short times and to monitor such changes over prolonged periods of time, and to do so at particularly low cost making the method practical for widespread use.

SUMMARY OF THE INVENTION

The method for mapping internal body tissue of the present invention solves the aforementioned problems and meets the aforementioned needs by determining the spatial distribution of bone tissue of a patient that shields target soft tissue the structure of which it is desired to determine and monitor, and subjecting the patient to changing electric, magnetic or electromagnetic fields adapted for interacting with the target soft tissue as a function of the spatial distribution of the soft tissue. Electric, magnetic or electromagnetic energy that is transmitted through the bone and the soft tissue is analyzed to infer the spatial distribution of the soft tissue with the assistance of knowledge of the spatial distribution of the bone tissue.

Therefore, it is a principal object of the present invention to provide a novel and improved method for mapping internal body tissue.

It is another object of the present invention to provide a method for mapping internal body tissue that provides for the ability to discern structural changes in the body tissue that occur over very short times.

It is yet another object of the present invention to provide a method for mapping internal body tissue that provides for the ability to monitor such changes over prolonged periods of time.

It is still another object of the present invention to provide a method for mapping internal body tissue that provides for the ability to discern structural changes in the body tissue that occur over very short times and to monitor such changes over prolonged periods of time.

It is a further object of the present invention to provide a method for mapping internal body tissue that provides for any or all of the aforementioned objects at particularly low cost.

The foregoing and other objects, features and advantages of the present invention will be more readily understood upon consideration of the following detailed description of the invention, taken in conjunction with the following drawings.

BRIEF DESCRIPTION OF THE DRAWING

The FIGURE is a schematic of an apparatus for carrying out the method for mapping internal body tissue according to the present invention.

DETAILED DESCRIPTION OF A PREFERRED EMBODIMENT

As mentioned above, the present invention addresses a recognition of the present inventor, that at least brain soft tissue, and probably other soft tissue in the body, can exhibit changes to its structure during a short time-span, which can be as short as a few tens of milliseconds, in response to certain pathologies. This recognition has led the present inventor to a method for mapping internal body tissue that is able to discern structural changes therein that occur over very short times and to monitor such changes over prolonged periods of time, and to do so at particularly low cost making the method practical for widespread use.

According to the invention, the inventor's geodesic sensor net described in U.S. Pat. No. 5,291,888, incorporated by reference herein in its entirety, is preferably employed in a method analogous to the method for localizing electrical activity in the body described in the inventor's U.S. Pat. No. 6,330,470, also incorporated by reference herein in its entirety. Among other things, the application discloses the integration of externally applied imaging signals, such as injected currents for measuring tissue conductivity, with analysis of the body's spontaneous electromagnetic signals. The sensor net as described in the '888 Patent is particularly well adapted for use with approximately spherical body parts such as the head, while a preferred method for spatially distributing the sensors over a body surface of generalized shape is described in the inventor's U.S. patent application Ser. No. 09/645,026, also incorporated by reference herein in its entirety.

Signal producing elements 12 are distributed over the surface of a target body part 10, preferably according to the aforementioned methods to achieve maximum resolution. Input signals produced by the signal producing elements 12 are transmitted through or scattered by the interior tissues of the body part to varying degrees depending on the type of tissue and its density as a function of location in space. Sensors 20 to receive the input signals as modified by the tissue (hereinafter "output signals") are also preferably distributed over the surface of the target body part according to the aforementioned methods. Both input and output signals may be direct or induced currents or voltages. For example, the signals may be currents applied to or received from the skin directly, or may be electromagnetic waves applied to or received from the skin by radiant propagation.

According to well known methods, the received output signals provide a spatial distribution of intensity that, when related to the spatial distribution of the input signals, provides information about the spatial distribution, within the body, of the various tissue types. A finite element model of the tissue in the body volume is constructed in three dimensions, the input signals are modeled, and the output voltages are simulated by computer. The characteristics of the various tissue types in the body volume are assumed and their densities as a function of location are varied from selected starting points until accordance is made with the data received from the sensors to a desired degree of resolution.

According to the invention, a transfer function may then be defined that describes the relationship between the input signals as produced by the signal producing elements and the output as sensed by the sensors. The transfer function is in general the superposition of a transmissivity "T" for the signal appropriate for each tissue structure multiplied by a corresponding density function "D" defining the density of that tissue structure as a function of spatial coordinates.

The transmissivity T is in general a complex constant for a given tissue structure, though it may be a function of time for a given tissue type since the tissue is presumed to be susceptible to pathologies that may change its structure over time as noted previously. The density D is in general a matrix of coefficients.

For purposes herein, bone is defined to have a transmissivity $T_b$, grey matter (brain cells) a transmissivity $T_g$, and white matter (nerve fibers) a transmissivity $T_w$. These tissue types apply particularly to mapping brain tissue. The transmissivities for other tissue types would be likewise defined for other body structures including other cranial tissue.

Also for purposes herein, for a particular subject's head, the density of bone is $D_b$, the density of grey matter is $D_g$, and the density of white matter is $D_w$.

Accordingly, the transfer function for this subject's head is $(T_b \cdot D_b)+(T_g \cdot D_g)+(T_w \cdot D_w)$ for a given spatial distribution of signal producing elements and sensors. The transmissivities may be determined in a laboratory, in advance of any application of the method to a particular patient. However, all of the density functions are unknowns and each generally has multiple coefficients. Therefore, in practice, the solution to the problem of determining the density functions that could produce the measured outputs given the known inputs (hereinafter "inverse problem") is a difficult problem to solve, hence it is demanding of computer time. Moreover, all else being equal, the resolution and certainty that can be obtained from the solution is limited by the number of unknowns.

The present inventor has recognized that bone tissue does not change structure on a short time scale like soft tissue. Therefore, according to the invention, a static imaging method such as X-ray CT is preferably employed to determine $D_b$, providing the outstanding advantage of fixing this function to significantly decrease the number of unknowns that must be accounted for in the problem solution. Other methods for static imaging of a particular subject's bone density may be employed as well without departing from the principles of the invention. For example, the subject's bone density may be determined by observing changes in an MRI signal that result from an impressed electrical current. As an alternative to imaging a particular subject, $D_b$ may be estimated by comparison of the subject to a database of previously obtained bone density functions linked by subject attributes such as but not limited to head geometry, height, weight, age, sex and race. Once $D_b$ is determined for a particular subject, it need not be determined again for most purposes.

On the other hand, it is an aim of the present invention to map soft tissue such as grey and white matter tissue as a function of time. Therefore, according to the invention, the computer is used to solve the problem for the remaining unknowns, where the problem is now reduced in scope to matching the measured ratio of signal output to signal input with the transfer function $K_1+(K_2 \cdot D_g)+(K_3 \cdot D_w)$, where the K's are in general complex constants for a given instant in time. This inverse problem is easier to solve, leading to increased speed, increased resolution, and increased confidence in the results.

Nevertheless, for present day computers of reasonable cost, the computational time required to solve the problem remains significantly longer than the few tens of milliseconds during which structural changes are anticipated to take place. Accordingly, the recognition of an important structural change may await some time delay; however, minimizing this delay as provided by the present invention may be crucial. Further, signals may be recorded over time and the transfer function over selected periods of time may be constructed after an event. Again, while some delay in identifying structure or structural changes may be necessary, minimizing this delay may still be of great use to permit responding more quickly to a patient's needs. Still further, the structural changes of concern are generally not large and are generally localized in a relatively small region of space. Therefore, the functions $D_g$ and $D_w$ may not change to a great degree over time, so that perturbation methods may be used to solve the inverse problem more rapidly.

In the preferred embodiment, at least one and preferably both of two sets of the signals are employed. One of the sets of signals is an electromagnetic wave in the near-infrared. The other of the sets of signals is directly applied electrical current in the kilohertz frequency range. These sets of signals are believed to interact similarly with tissue, so that the transfer functions and therefore the solutions to the inverse problem are not substantially different in general. However, these sets of signals do not interact identically with tissue, and may interact substantially differently with respect to particular tissues, so that the use of both sets of signals together provides a further means to distinguish or resolve the tissues.

Also according to the invention, in like manner to that described above, bone density information may be used to increase the power to analyze signals produced by or otherwise emanating from the body tissue, such as EEG (electroencephalographic), MEG (magnetoencephalographic) and ECG (electrocardiographic) signals. Further, the use of bone density information may be employed for analyzing any combination of such signals along with any combination of applied signals, potentially providing important convergent information on the rapid changes in neural tissue in both normal and pathological function. Regardless of the number of signals for which the bone density information is to be used, the bone density information reduces the number of unknowns in the solution of the inverse problem.

It is to be recognized that, while a particular method for mapping internal body tissue has been shown and described as preferred, other configurations could be utilized, in addition to configurations already mentioned, without departing from the principles of the invention.

The terms and expressions which have been employed in the foregoing specification are used therein as terms of description and not of limitation, and there is no intention of the use of such terms and expressions of excluding equivalents of the features shown and described or portions thereof, it being recognized that the scope of the invention is defined and limited only by the claims which follow.

What is claimed is:

1. A method for mapping tissue of a body, the tissue being at least partially shielded by bone, comprising:
    (a) determining the density of the bone as a function of spatial coordinates;
    (b) applying a first input signal to the tissue through the surface of the body;
    (c) measuring a first output signal representing said input signal as modified by the tissue;
    (d) determining a relationship between said input signal and said output signal, said relationship being a function of the density of the bone as well as the density of the tissue; and
    (e) employing the result of step (a) in step (d) to reduce the number of unknowns in said step (d).

2. The method of claim 1, wherein step (a) further comprises irradiating the bone with input X-rays, measuring a second output signal representing said input X-rays as modified by the bone, and determining a relationship between said input X-rays and said second output signal, said relationship being a function of the density of the bone.

3. The method of claim 2, wherein, in step (b), said input signal is a current directly applied to the skin.

4. The method of claim 2, wherein, in step (b), said input signal is an electromagnetic wave in the near-infrared.

5. The method of claim 3, further comprising (f) applying a second input signal to the tissue through the surface of the body, wherein step (d) further comprises determining a relationship between said second input signal and said output signal, said relationship being a function of the density of the bone as well as the density of the tissue.

6. The method of claim 5, wherein, in step (f), said second input signal is an electromagnetic wave in the near-infrared.

7. The method of claim 4, further comprising (f) applying a second input signal to the tissue through the surface of the body, wherein step (d) further comprises determining a relationship between said second input signal and said output signal, said relationship being a function of the density of the bone as well as the density of the tissue.

8. The method of claim 7, wherein, in step (f), said second input signal is a current directly applied to the skin.

* * * * *